United States Patent
Penny et al.

(10) Patent No.: US 7,818,184 B2
(45) Date of Patent: Oct. 19, 2010

(54) PATIENT MEDICAL FLUID PARAMETER DATA PROCESSING SYSTEM

(75) Inventors: Mark Penny, Salem, MA (US); Alan Alpert, Charlestown, MA (US); Rand J. Monteleone, Acton, MA (US)

(73) Assignee: Draeger Medical Systems, Inc., Andover, MA (US)

( * ) Notice: Subject to any disclaimer, the term of this patent is extended or adjusted under 35 U.S.C. 154(b) by 2189 days.

(21) Appl. No.: 10/411,056

(22) Filed: Apr. 10, 2003

(65) Prior Publication Data

US 2004/0055611 A1 Mar. 25, 2004

Related U.S. Application Data

(60) Provisional application No. 60/413,033, filed on Sep. 24, 2002.

(51) Int. Cl.
- A61B 5/00 (2006.01)
- G06F 19/00 (2006.01)
- G06F 17/00 (2006.01)
- G06Q 10/00 (2006.01)
- G06Q 50/00 (2006.01)

(52) U.S. Cl. ............................ 705/3; 705/2; 700/90
(58) Field of Classification Search ............... 700/90; 705/2, 3
See application file for complete search history.

(56) References Cited

U.S. PATENT DOCUMENTS

| | | | | |
|---|---|---|---|---|
| 4,504,263 A | * | 3/1985 | Steuer et al. | 604/65 |
| 4,652,120 A | * | 3/1987 | Sell | 356/28 |
| 4,898,578 A | | 2/1990 | Rubalcaba, Jr. | 604/66 |
| 4,994,671 A | * | 2/1991 | Safinya et al. | 250/255 |
| 5,045,069 A | * | 9/1991 | Imparato | 604/253 |
| 5,091,863 A | * | 2/1992 | Hungerford et al. | 700/283 |
| 5,190,522 A | | 3/1993 | Wojcicki et al. | 604/65 |
| 5,421,211 A | * | 6/1995 | Heckman | 73/861.25 |
| 5,578,005 A | | 11/1996 | Sancoff et al. | 604/82 |

(Continued)

FOREIGN PATENT DOCUMENTS

EP 0 960 627 A 12/1999

(Continued)

*Primary Examiner*—Neal R Sereboff
(74) *Attorney, Agent, or Firm*—Jack Schwartz & Associates, PLLC

(57) ABSTRACT

A system extrapolates and interpolates patient fluid intake or output parameter values and associated cumulative values over variable time intervals from a reduced set of stored fluid parameter values affecting fluid cumulative volume computation or rate of fluid intake or output computation. The extrapolation and interpolation function accomodates drip (continuing) fluid volumes as well as supplemental (non-continuing e.g., bolus) fluid volumes. A patient medical parameter data processing system provides patient medical parameter data for trend indicative display covering a time period comprising user selectable patient parameter acquisition time intervals. The system includes an acquisition processor for receiving data identifying, for a continuing infusion, rate of volume of fluid infusion into a patient, a fluid type identifier and a start time and start date of said continuing infusion. The received data also identifies for a non-continuing infusion, a total volume of fluid infusion, a fluid type identifier and a time and date of the non-continuing infusion. A data processor determines, from the received data, a cumulative total volume infusion of a particular fluid into a particular patient for a particular user selectable patient parameter acquisition time interval.

21 Claims, 11 Drawing Sheets

U.S. PATENT DOCUMENTS

| | | | |
|---|---|---|---|
| 5,772,635 A * | 6/1998 | Dastur et al. | 604/131 |
| 5,910,135 A | 6/1999 | Hadzic et al. | 604/251 |
| 6,083,206 A * | 7/2000 | Molko | 604/253 |
| 6,213,972 B1 | 4/2001 | Butterfiled et al. | 604/67 |
| 6,416,291 B1 | 7/2002 | Butterfield et al. | 471/44.2 |
| 6,622,572 B2 * | 9/2003 | Kobayashi et al. | 73/861.29 |
| 6,968,851 B2 * | 11/2005 | Ramirez et al. | 137/1 |
| 2002/0061255 A1 | 5/2002 | Nguyen et al. | 417/478 |
| 2002/0077852 A1 | 6/2002 | Ford et al. | 705/2 |
| 2002/0107476 A1 | 8/2002 | Mann et al. | 604/67 |
| 2002/0183693 A1 * | 12/2002 | Peterson et al. | 604/151 |
| 2002/0193679 A1 * | 12/2002 | Malave et al. | 600/407 |
| 2003/0048185 A1 | 3/2003 | Citrenbaum et al. | 340/540 |

FOREIGN PATENT DOCUMENTS

| | | |
|---|---|---|
| EP | 1 178 288 A1 | 2/2002 |

* cited by examiner

US 7,818,184 B2

PATIENT MEDICAL FLUID PARAMETER DATA PROCESSING SYSTEM

This is a non-provisional application of provisional application Ser. No. 60/413,033 by A. Alpert filed Sep. 24, 2002.

FIELD OF THE INVENTION

This invention is related to processing and displaying patient medical information in a network environment and in particular to facilitating storage, retrieval and processing of data for fluid intake and output computations and display.

BACKGROUND OF THE INVENTION

Patient medical parameter data is acquired, collated, stored and displayed for use in providing patient clinical care in hospitals, clinics, and other healthcare delivery settings. Patient medical parameter data may include vital signs ventilator information, infusion pump data associated with fluid delivery and other data. Such patient medical parameter data is typically displayed on a patient monitoring device screen in a trend indicative chart with a time axis. This type of chart is commonly termed a Flowsheet. A patient monitoring device is usually located at a patient bedside or nursing station in a hospital ward or in an intensive care, surgical or other location and may be connected to a network such as the Internet, a LAN, a WAN or an intra-net for acquiring patient parameter data from local sources (e.g., patient attached sensors) or remote sources (e.g., a remotely stored electronic patient record). The Flowsheet is an electronic chronological chart of patient parameter information that substitutes for a paper vital sign Flowsheet.

It is desirable that an electronic Flowsheet offer similar or better features and flexibility than a paper Flowsheet chart that it replaces. Therefore an electronic Flowsheet needs to enable healthcare personnel to acquire and record patient Fluid Intake and Output related parameters including infusion pump data associated with fluid delivery and other information. Known systems typically acquire, collate and store Fluid related patient medical parameter data for display in a Flowsheet within corresponding parameter acquisition time intervals together with a time axis. For this purpose, known systems acquire and store large quantities of patient medical parameter data over relatively long time periods (e.g., for the duration of a patient hospital stay) for display in relatively short Flowsheet acquisition time intervals (e.g., 3 minutes to a few hours). Typically at least one patient parameter value is acquired for each acquisition time interval. This results in the acquistion of extensive data sets containing redundant data requiring the allocation of correspondingly large amounts of memory. In addition, acquired fluid intake or output data values are used in computation and display of cumulative patient fluid intake or output values. Consequently, if a previously recorded fluid intake or output data value used in such a computation is changed, a series of subsequent computed fluid cumulative values need to be re-computed and updated for Flowsheet display. Such a change in a prior fluid intake or output data value occurs in response to a user, such as a nurse, administering a fluid medication and manually entering a corresponding fluid intake or output value overriding an existing value, for example. The difficulty involved in re-computing fluid cumulative intake or output values over a time period (or updating cumulative values within individual parameter acquistion time intervals) is compounded by the large quantity of data involved. A system according to invention principles addresses these problems and derivative problems.

SUMMARY OF THE INVENTION

A system extrapolates and interpolates patient fluid intake or output parameter values and associated cumulative values over variable time intervals from a reduced set of stored fluid parameter values affecting fluid cumulative volume computation or rate of fluid intake or output computation. The extrapolation and interpolation function accomodates drip (continuing) fluid volumes as well as supplemental (non-continuing e.g., bolus) fluid volumes. A patient medical parameter data processing system provides patient medical parameter data for trend indicative display covering a time period comprising user selectable patient parameter acquisition time intervals. The system includes an acquisition processor for receiving data identifying, for a continuing infusion, rate of volume of fluid infusion into a patient, a fluid type identifier and a start time and start date of said continuing infusion. The received data also identifies for a non-continuing infusion, a total volume of fluid infusion, a fluid type identifier and a time and date of the non-continuing infusion. A data processor determines, from the received data, a cumulative total volume infusion of a particular fluid into a particular patient for a particular user selectable patient parameter acquisition time interval.

DETAILED DESCRIPTION

Figure 1:
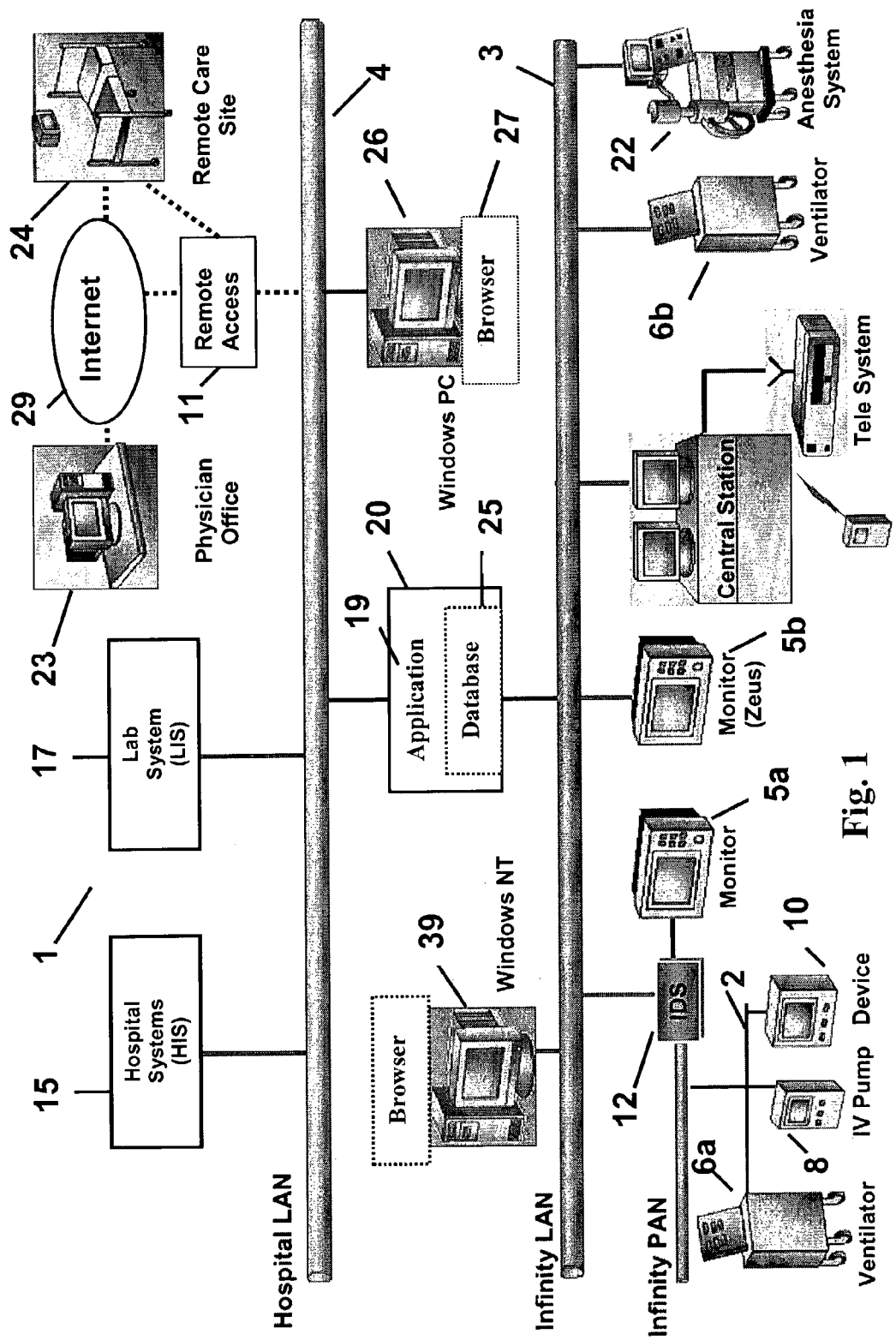
FIG. 1 is a block diagram of a communication network with various devices including a system for storing a reduced set of fluid parameter values, according to the principles of the invention.

A system and user interface calculates and displays Flowsheet trend indicative Patient Fluid input and output data, cumulative fluid information and data identifying net input or output fluid balance volumes over user selectable variable time periods. The system advantageously stores a reduced set of fluid parameter values affecting fluid cumulative volume computation or rate of fluid intake or output computation and excludes other data. Fluid volume data is dynamically calculated from the reduced data set in response to a command to display a trend indicative Flowsheet display (including fluid volume data) i.e. at display generation run time. As a result, user change or alteration of past data point values within the reduced data (e.g., to replace a data point value with a value determined to be more accurate), does not result in change of a series of subsequent stored data values. The volume data is dynamically extrapolated and interpolated from the reduced data set for display using a predetermined algorithm in response to a user command to initiate display generation. This advantageously eliminates the need for storing redundant intermediate Fluid volume data values that are inconsequential to the computation of patient fluid cumulative volumes or computation of rate of fluid intake or output. The dynamic extrapolation and interpolation of volume data prior to Flowsheet volume data display also eliminates the need to update an extensive series of stored fluid volume data values in response to user alteration of a prior fluid volume data value. The system advantageously avoids storage and modification of large quantities of fluid volume data and supports extrapolation and interpolation of intermediate Fluid volume data values for display in user selectable Flowsheet acquisition time intervals without requiring update of stored fluid parameter data sets.

Known Flowsheet display systems typically establish a minimum time interval during which patient parameters are acquired (a patient parameter acquisition time interval) and store a data point for each time interval. This results in burdensome accumulation, storage, maintenance and processing of large quantities of patient parameter data. Further, in such known systems, if a user modifies a previously acquired data value (e.g., a fluid volume value) associated with a particular acquisition time interval, a series of subsequent successive data values (e.g., cumulative volume or net balance data) needs to be updated to reflect the modification. In contrast a system according to invention principles extrapolates and interpolates patient fluid intake or output parameter values and associated cumulative values over variable time intervals, from a reduced data set in response to a user command to initiate display generation. The system advantageously extrapolates and interpolates fluid volumes over user selectable variable time periods using a reduced data set including data identifying, fluid type, change in fluid volume intake and output rates, and supplemental (e.g., one-time, non-continuing, supplemental infused bolus) fluid volumes and associated occurrence times. Consequently, the reduced data set advantageously just stores data changes to fluid volume intake and output rates, volumes, and associated times identifying when changes occured. Further, the system extrapolates and interpolates new volume data at display generation run time based on the reduced data set, thereby the system readily accommodates alteration of a historical fluid data value and time period without involving burdensome re-computation and update of a series of historical interdependent data values. The Fluid data extrapolation and interpolation is performed using an algorithm and a database incorporating the reduced data set together with a compatible database interface.

FIG. 1 is an exemplary block diagram of a communication network incorporating server 20 hosting executable application 19 providing a trend indicative user interface display of patient parameters (termed a Flowsheet) encompassing identified acquisition time intervals. A Flowsheet may display different types of parameters associated with, for example, Intra-Venous fluids, drip administered medications, blood products, blood pressure, ventilation, vital signs, blood oxygen concentration, and infusion pump fluid delivery. Particular parameters contain different pieces of data that are important to describe a particular fluid. Further, hospitals typically employ different practices concerning the data to be included with each parameter and the manner of displaying this data. A system executed by application 19 advantageously stores a reduced fluid parameter data set for use in calculating and displaying Flowsheet Patient Fluid input and output data, cumulative fluid information and data identifying net input or output fluid balance volumes over user selectable variable time periods at display generation run time.

In an alternative embodiment, the executable application providing the Flowsheet user interface may be resident in another processing device in any part of the network shown in FIG. 1. Communication network 1 (FIG. 1) is represented by an IP (Internet Protocol) compatible network with a hierarchy of local area and wide area networks interconnected together. It is to be noted that although the present exemplary hospital or medical network is an IP compatible network, other types of networks such as, but not limited to optical or wireless networks, using other computing protocols such as, but not limited to, for example, X.25, frame relay, IBM SNA etc., may also be used, as one skilled in the art can readily appreciate. In addition, although the exemplary network described is a hierarchical network, this is not required by the present invention. Any type of network architecture that provides communication connectivity among the devices on the network may be used.

As shown in FIG. 1, the first level of the exemplary hierarchical network 1 comprises a Medical Interface Bus (MIB) 2. A MIB is a well-known medical industry standard for locally connecting medical devices together. As shown in FIG. 1, MIB 2 is typically used to interconnect medical devices in a care unit such as a patient's room within a nursing station to administer care to a particular patient and to monitor the particular patient. Various medical devices may be connected via MIB 2; examples shown in FIG. 1 comprise a ventilator 6a, IV (Intravenous) Pump 8 or other medical equipment 10. MIB 2 is typically connected to a second level LAN network 3 through an Interface Docking Station (IDS) device 12, for interfacing to Ethernet-compatible LAN network 3. The LAN 3 may be for example, an Infinity LAN, marketed by Siemens Medical System. This higher-level LAN 3 is typically, though not necessarily, used by other care units such as a particular department within a hospital, such as an intensive care unit or surgery unit, etc., depending on the size of the organization.

Although not shown in FIG. 1, more than one MIB may be connected to the second level LAN 3, so that more than one patient may be monitored or provided with care through LAN 3. In addition, medical devices may be connected directly to higher-level LAN 3. For example, as shown in FIG. 1, a ventilator 6b and an anesthesia system 22 are connected directly to LAN 3, without use of a MIB. Furthermore, LAN 3 may be interconnected to a Hospital LAN backbone 4 which also is Ethernet compatible. This backbone network 4 provides communication connectivity between various departments within a hospital or medical organization; for example, connecting hospital administrative systems 15 together with laboratory systems 17. In addition, the Hospital LAN 4 has a remote access gateway 11 which provides remote, secured access from, for example, a remote doctor's office 23 or a remote care site 24, to the various systems and devices on network 1, through for example, Internet 29. Alternatively, a remote site may also access the remote access gateway 19 directly through, for example, a dial-up telephone port, ADSL, or other types of private connection. Remote access gateway 11 may also be part of server 20, to be described below, instead of standing alone, as well know in the art.

According to the principles of the present invention, executable application 19 (or multiple applications in another embodiment) resides on central server on LAN 3 for gathering and processing data from the peripheral medical devices or facilities coupled to LAN 3 or hospital LAN 4, including laboratory results supplied via laboratory system 17 connected through an HL7 interface, for example. Additional medical parameter data including additional laboratory results acquired from any number of medical devices such as those shown in FIG. 1 may be obtained by server 20 using ASTM messaging, for example. The acquired medical parameters associated with a given patient, including laboratory test results, are acquired from the medical devices on network 1 for display and control on monitors 5a, 5b or PCs 26 and 39 or any other display hosting device at any level of the FIG. 1 network. One skilled in the art can readily recognize that server 20 may reside at any level of the hierarchy of network 1, since all the different levels of LANs (e.g., 3, or 4), as well as remote sites in FIG. 1 are interconnected. An example of server 20, is a Chart Assist server, marketed by Siemens Medical System. The server may be hosted, for example, by a computer system that is capable of running Microsoft Windows operating system. Application 19 provides a user interface trend indicative display of patient parameters (a Flowsheet) covering a time period comprising user selectable acquisition time intervals. A user selectable acquisition time interval represented by a column in the Flowsheet covers a time period (typically 3 minutes to 4 hours or another user selectable range) in which patient parameters are acquired.

Figure 2:
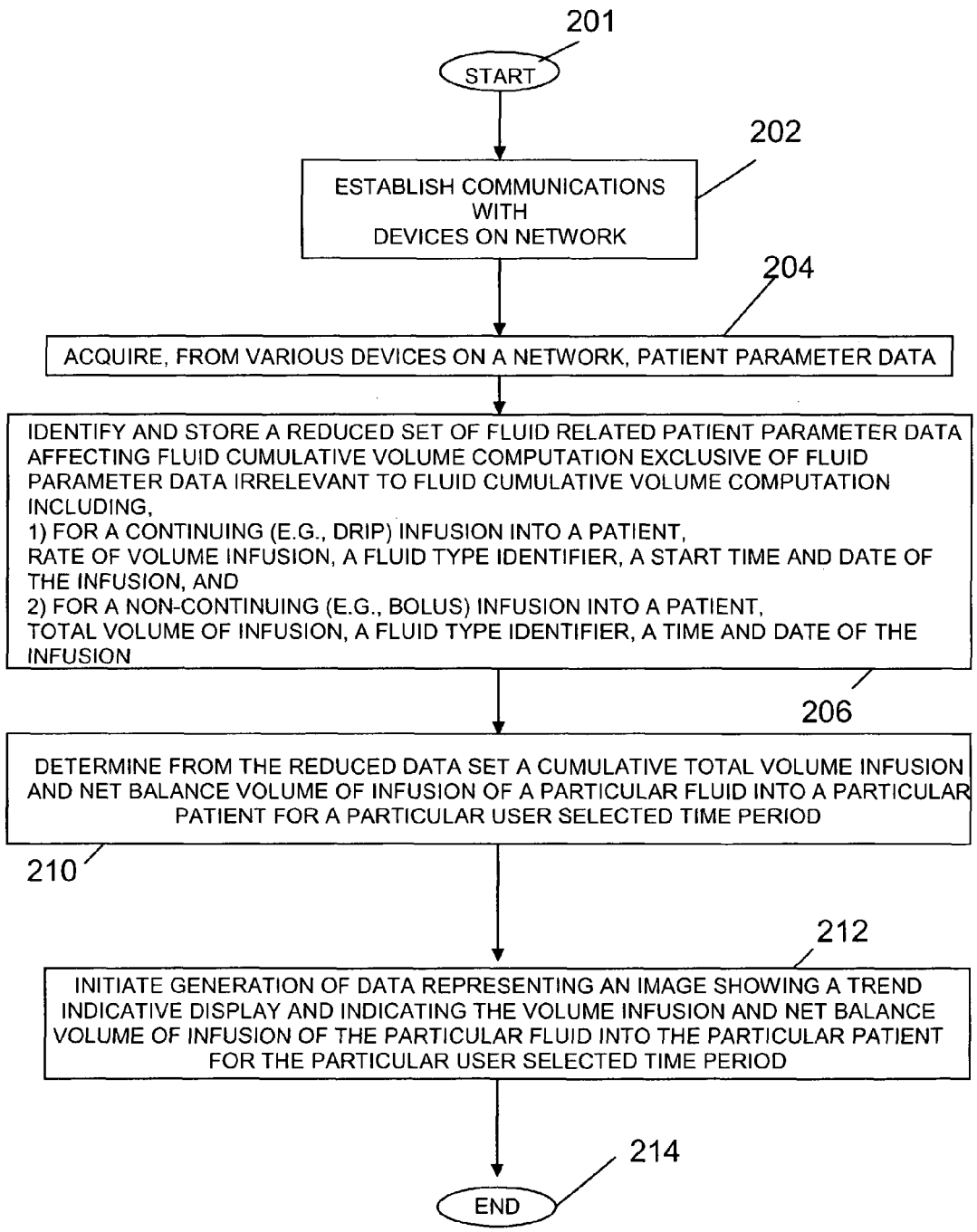
FIG. 2 represents a flowchart of a method for deriving fluid intake or output parameter values and associated cumulative values over variable time intervals from a reduced data set, according to the principles of the invention.

FIG. 2 shows in flow chart form, functions that are performed by executable application 19. Application 19 establishes communication with devices on the network as shown in step 202 after the start at step 201. This is done, for example, by using IP protocol and the known IP device address for each device on the network 1 (FIG. 1), in conjunction with any higher application-layer protocols, as known in the art. Once communication is established between server 20 and the other devices, application 19, in step 204, starts to acquire parameters that are being monitored, laboratory results and settings selected for the various devices. As previously mentioned, laboratory results may be obtained through an HL7 interface with LIS 17, or via ASTM or MIB point of care (POC) medical devices depicted in FIG. 1. Fluid and other parameters may also be acquired by user data entry. Types of acquired monitored patient parameters include, blood pressure parameters, respiratory or ventilation parameters, vital sign parameters, blood oxygen concentration representative parameters, infusion pump parameters associated with fluid delivery, continuing infusion drip related parameters, non-continuing bolus infusion related parameters and other fluid related parameters.

Medical data and laboratory results may be continuously, periodically or non-periodically acquired and correlated with a given patient for storage in relational data base 25 within server 20. Data base 25 may be of the type used for storing relational data such as the Microsoft SQL server. In addition, application 19 may obtain patient parameter data and patient data comprising medical laboratory results that are first entered and stored, for example, in laboratory system 17 of FIG. 1. Also, application 19 may acquire healthcare provider entered medical notes for display. In step 206, application 19 identifies and stores a reduced set of acquired fluid related patient parameter data affecting rate of fluid intake or output computation or fluid cumulative volume computation and excluding fluid parameter data irrelevant to rate of fluid intake or output computation or fluid cumulative volume computation. The reduced set of fluid related patient parameter data includes for a continuing infusion, rate of volume of fluid infusion into a patient, a fluid type identifier and a start time and start date of the continuing infusion. Similarly, the reduced set of data includes for a non-continuing infusion (e.g., a supplemental bolus infusion volume), a total volume of fluid infusion, a fluid type identifier and a time and date of the non-continuing infusion. Application 19 in step 210 determines (by interpolation or extrapolation), using the reduced data set, a fluid volume infusion, a cumulative total volume infusion and net infusion fluid balance of a particular fluid into a particular patient for a particular user selected time period comprising one or more user selectable patient parameter acquisition time intervals. The user selected time period may comprise, a number of minutes, an hour, a multiple hour interval, a day and a work shift period. Further, in another embodiment, application 19 also interpolates or extrapolates a rate of volume infusion.

Application 19 in step 210 determines the fluid volume related data using an extrapolation and interpolation algorithm employing input data comprising the continuing infusion and non-continuing infusion fluid data of the reduced data set stored in step 206. An exemplary algorithm follows. In this algorithm, an input value for a continuing infusion is a rate of volume of fluid infusion into a patient and an input value for a non-continuing infusion (supplemental or bolus infusion volume) is a value of a total volume of fluid infusion. Further, within the algorithm, an input value time is the time an input value was entered (rate of volume of fluid infusion value or value of a total volume of fluid infusion). A rate of volume of fluid infusion is set at a particular time, e.g., 1000 cc saline at 250 cc/hr started at 11:00 am Feb 12, 2002. A supplemental or bolus fluid volume into or out of a patient is also associated with a particular input or output time, e.g., an injection of 100 cc of a medication at 11:00 am Feb. 13, 2002 or an empty 1000 cc fluid output container recorded at 10:00 am Feb. 14, 2002. Further, a fluid output rate is indicated as a negative rate. The algorithm stores a non-continuing infusion total volume value separately from a continuing volume infusion value derived using volume rate data in order to enable separate display of these different items in different display modes. Algorithm:

```
Initial current infusion volume and volume infusion rate are zero
(corresponding to the beginning of a patient stay, for example).
    For each input value (from the first to the last within a time period
for which fluid volume data is to be computed)
        if the input value time falls within the current interval then
            calculate the volume for this interval up to this
input time using the current rate
            add the volume to this interval's total volume
            if this input has a rate change
                make this input's rate be the current rate
            end if
            if this input has a bolus volume
                add to the volume from bolus for this
interval
            end if
        else if the input value time is after the current interval
            calculate the volume for the current interval to the
end of the interval using the current rate
            add the volume to the interval's total volume
            while the input value time is after the current
interval
                increment the current interval (and output
to display buffer)
                calculate the volume for the interval using
the current rate
                store the volume for the interval
            end while
            calculated the volume for this interval up to this
input time using the current rate
            add the volume to this interval's total volume
            if this input has a rate change
                make this input's rate be the current rate
            end if
            if this input has a bolus volume
                add to the volume from bolus for this
```

-continued

```
        interval
            end if
        end if
    Next input value
End of Algorithm.
```

Application 19 employs the algorithm to create cumulative fluid infusion (and output) volume data and net balance of fluid infusion data of fluids into (and out of) a patient for a user selectable time period comprising one or more parameter acquisition time intervals such as for an entire patient hospital stay. The algorithm processes data in the reduced data set accumulated for individual parameter acquisition time intervals (e.g., an hour). The algorithm uses changes in, rate of fluid infusion or output or of input or output volumes and the time of such changes within the time period of the hospital stay to be examined, for example. A user further selects a portion of the created data for display and examination in a selectable display mode in step 212 (FIG. 2). Specifically, application 19 in step 212 initiates generation of data representing a Flowsheet image showing a trend indicative display and indicating, the fluid volume infusion, the cumulative total volume infusion and net infusion fluid balance into a particular patient of a particular fluid for the user selected time portion.

In response to user selection of a second time period comprising one or more acquisition time intervals, application 19 automatically determines and displays, in steps 210 and 212, another volume, cumulative total and net balance infusion of the particular fluid into the particular patient for the second time period using the reduced data set. A user may use a Microsoft Windows compatible PC 26 or Windows NT compatible PC 39 as shown in FIG. 1, or any other processing devices capable of running a menu generating program such as a web browser program 27 (e.g., Microsoft Internet Explorer or Netscape Navigator, etc.) to view a Flowsheet, medical parameters and laboratory results information associated with a given patient. That is, a user may use a web browser on any processing device, as long as a communication connection can be made to server 20 and application 19, to make requests and view information acquired and stored in data base 25. This is advantageous, since a doctor may for example, gain access to a Flowsheet or laboratory test results from, for example, a remote physician's office 23, without having to access a dedicated terminal. Of course, a user can simply use a keyboard and/or a mouse or any other user interface devices to enter a user selection or request on a user computer, as is known in the art. Application 19 is therefore capable of collating and formatting medical data to be compatible with, for example, HTML (HyperText Mark-up Language) programming language for displaying data on a web browser. Application 19 is also responsive to, for example, HTTP (HyperText Transfer Protocol) commands originated from a user's web browser for making a request. The process of FIG. 2 ends at step 214.

Figure 3:
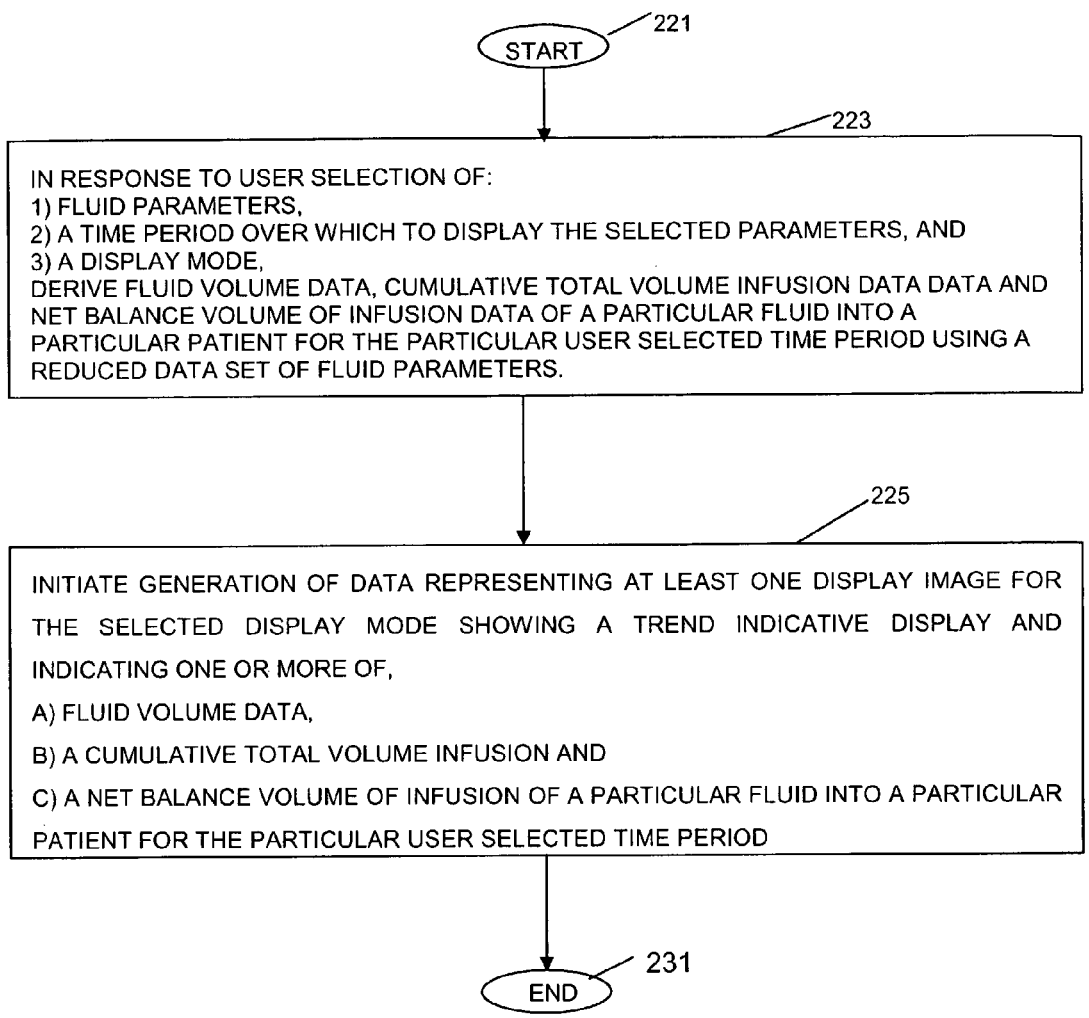
FIG. 3 represents a flowchart of a method for providing a user interface display of derived fluid intake or output parameter values and associated cumulative values over variable time intervals from a reduced data set, according to the principles of the invention.

FIG. 3 represents a flowchart of a method for providing a user interface for presenting derived fluid patient parameters. In step 223, following the start at step 221, application 19 receives Flowsheet configuration and user entered data identifying fluid parameters to be displayed, a display mode and a time period over which the selected fluid parameters are to be displayed. Application 19 in response to the received data, derives fluid volume data, cumulative total volume infusion data and net balance volume of infusion data of a particular fluid into a particular patient. In step 225, application 19 initiates generation of data representing at least one display image showing a trend indicative display including the derived volume data, cumulative total volume infusion data or net balance volume of infusion data of a particular fluid into a particular patient for the user selected time period. Specifically, application 19 initiates generation of data representing FIGS. 4-10.

Figure 4:
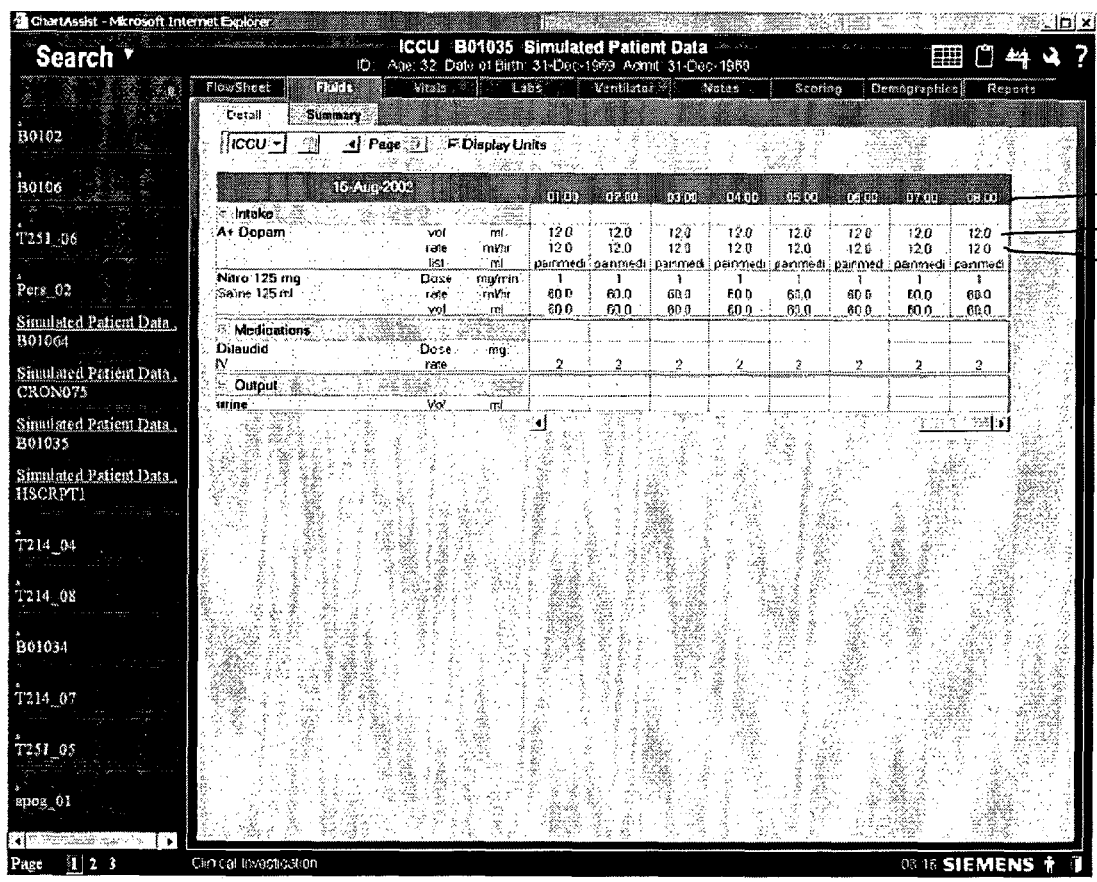
FIGS. 4-10 show user interface display images presenting derived fluid patient intake volume, cumulative volume and net fluid balance values over variable time intervals, according to the principles of the invention.
Figure 5:
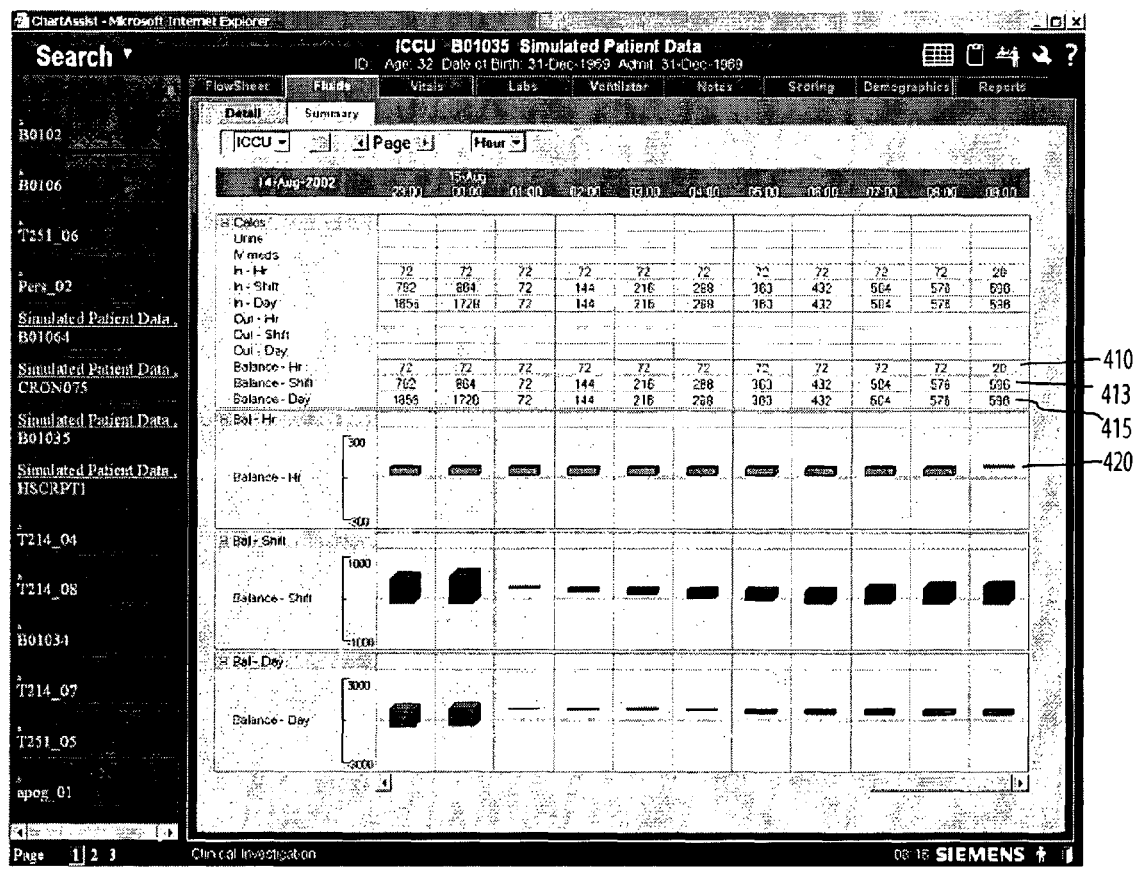

The display image of FIG. 4 shows total fluid input and output volumes 403 of a patient for individual hours (parameter acquisition time intervals) over a time period (01:00 to 08:00, item 405) together with fluid rates 407. The fluid volumes are computed by application 19 at 1 minute intervals. The display image of FIG. 5 shows patient net (input minus output) fluid balance volumes of a patient accumulated for hourly 410, work shift period 413 and daily 415 time periods and presented within columns of individual hourly parameter acquisition time intervals over a time period (23:00 to 09:00, item 417). The fluid volumes are computed by application 19 at 1 minute intervals. The cumulative fluid balance is presented in graphical format, e.g., hourly cumulative fluid net balance in window segment 420, advantageously enabling an accelerated evaluation of a patient fluid state by a clinician.

Figure 6:
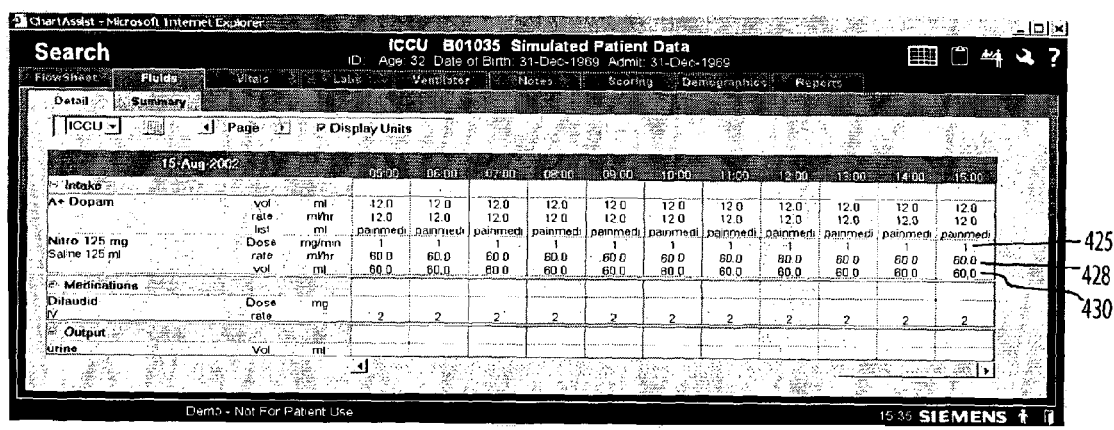
Figure 7:
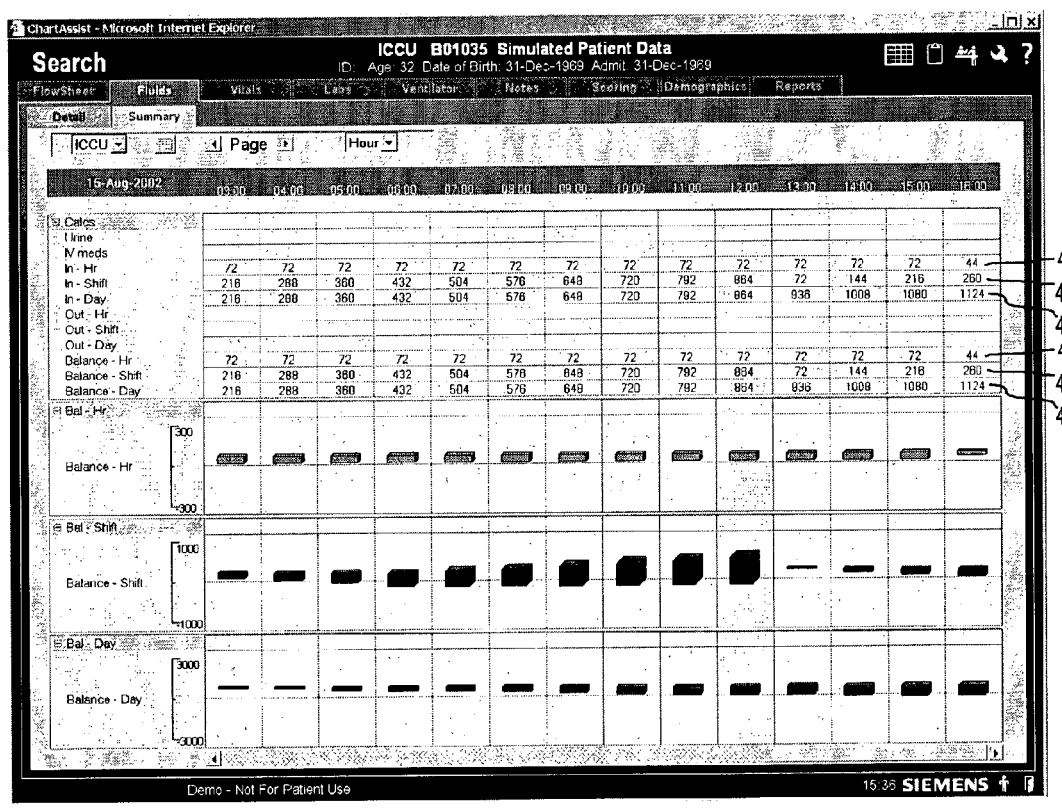
Figure 8:
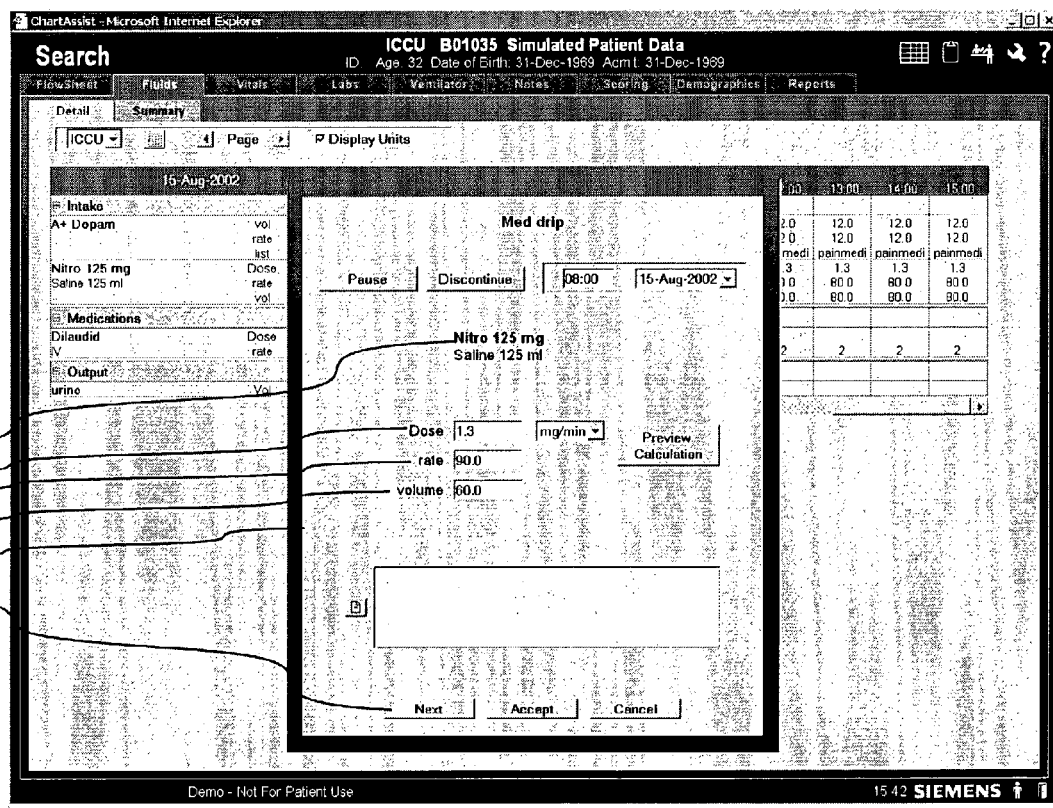
Figure 9:
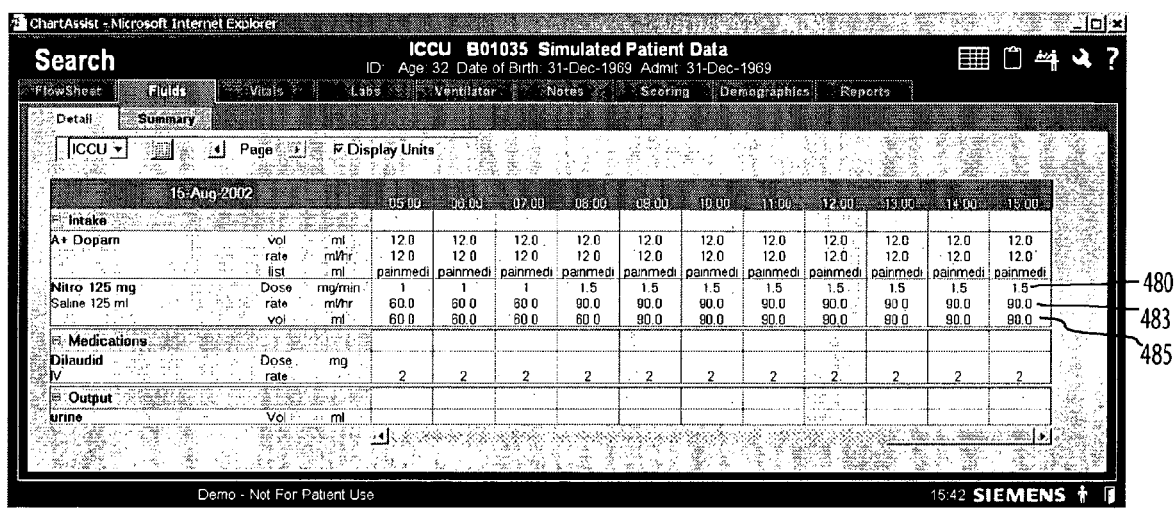
Figure 10:
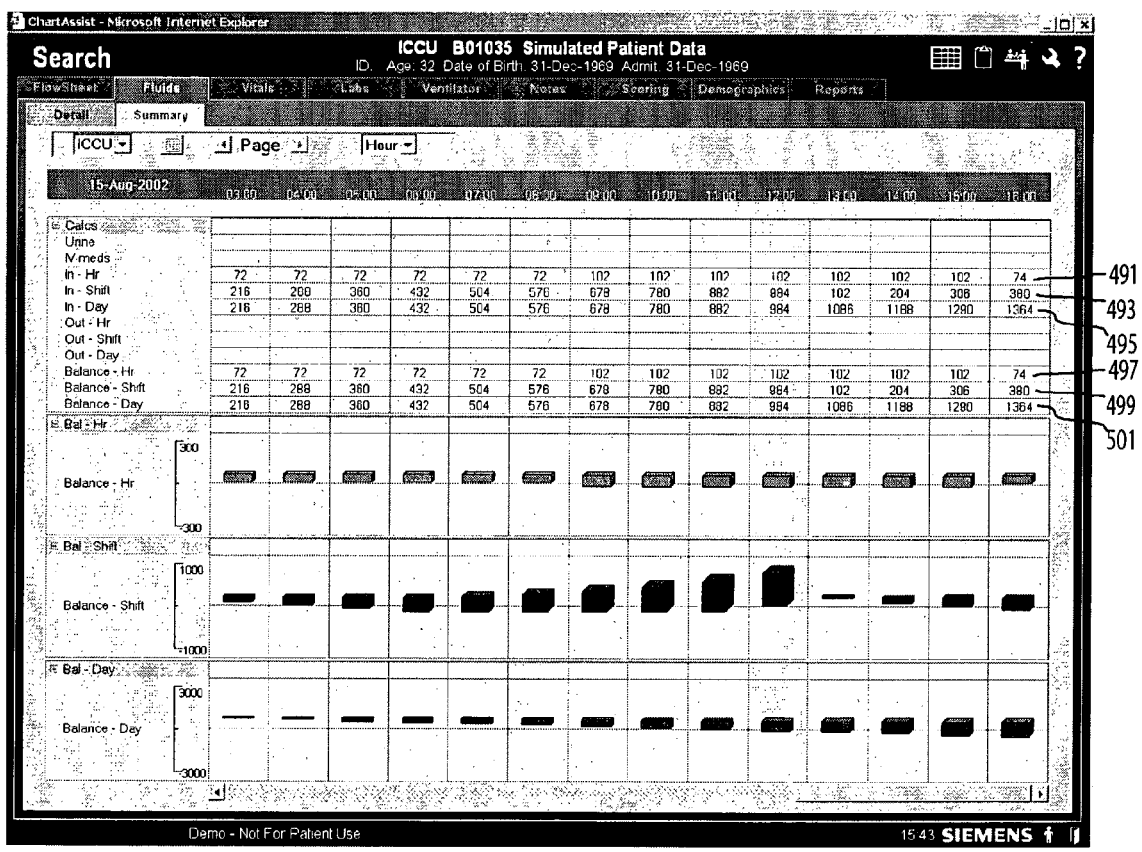

FIGS. 6-10 show a sequence of Flowsheet display images illustrating user editing of a fluid input rate and resultant recalculation of fluid cumulative volume totals and update of the display images to reflect the recalculated values. FIG. 6 shows a Flowsheet display image indicating fluid dose 425, fluid input rate 428 and fluid volume 430 for a medication medication determined for hourly time intervals. FIG. 7 shows a Flowsheet display image indicating fluid net volume input per hour 433, per work shift time period 436 and per day 439 as well as net fluid input balance per hour 441, per work shift time period 443 and per day 445 for an intra-venous medication determined for hourly time intervals. FIGS. 9 and 10 show Flowsheet display images corresponding to images of FIGS. 6 and 7 respectively but including recalculated fluid data following user alteration of fluid dose and fluid input rate data. Specifically, FIG. 9 shows the Flowsheet display image of FIG. 6 indicating fluid dose 480, fluid input rate 483 and fluid volume 485 following fluid data recalculation in response to a change in fluid dose, rate and volume occurring during an intermediate time interval (08:00). Similarly, FIG. 10 shows the Flowsheet display image of FIG. 9 following fluid data recalculation in response to a change in fluid input rate occurring during an intermediate time interval (09:00). Specifically, FIG. 10 indicates recalculated fluid net volume input per hour 491, per work shift time period 493 and per day 495 as well as net fluid input balance per hour 497, per work shift time period 499 and per day 501 for an intra-venous medication determined for hourly time intervals. Further, a user initiates generation of menu 459 of FIG. 8, to enter or modify fluid data of a fluid identified in item 467 and accept or cancel entries using menu bar 470. Specifically, menu 459 is used to modify or enter fluid input or output rate 463, a fluid input or output volume 465 and dose 460.

Application 19 in step 225 (FIG. 3), initiates generation of data representing a fluid parameter Flowsheet display image (e.g., as exemplified in FIG. 4) in response to a display mode selected in step 223. The fluid Flowsheet images of FIGS. 4 and 5 illustrate different display modes. In a further different display mode, application 19 generates a fluid Flowsheet incorporating two columns. A first column shows time (representing an associated time interval) and a second column shows a fluid volume accumulated in a corresponding time interval. The volume value is calculated from a fluid input or output rate of flow. In this display mode non-continuing supplementary (bolus) fluid volumes are not considered. Individual time intervals are presented on separate Flowsheet rows and a fluid volume value for an individual time interval is not carried forward for accumulation with a subsequent time interval fluid volume value.

In a further different display mode, application 19 generates a fluid Flowsheet incorporating a three column table. A first column includes time values representing time intervals (e.g., hourly intervals), a second column represents a total fluid volume accumulated during a corresponding time interval, and a third column (termed Parameter Instance) identifies the fluid concerned. The volume value is calculated from a fluid input or output rate of flow as well as from non-continuing supplementary (bolus) fluid volumes. Individual time intervals are presented in a single Flowsheet row and a fluid volume value for an individual time interval is carried forward for accumulation with a subsequent time interval fluid volume value so that fluid volume values are cumulative. An additional Flowsheet row is added in a further shift display mode to show fluid volumes accumulated during a work shift at an institution. Such a work shift time period is user configurable in duration and start time. During a work shift, fluid volumes accumulate in a similar manner to the time interval (e.g., hour volumes) but at the end of a shift, the fluid cumulative volume value is reset to zero and the first hour of the new shift has a single hour of accumulated fluid volume. Similarly, in a further display mode (a day display mode), an additional Flowsheet row is added to show fluid volume accumulated during individual 24 hour periods and the first hour of each new day has a single hour of accumulated fluid volume. The process of FIG. 3 ends at step 231.

Figure 11:
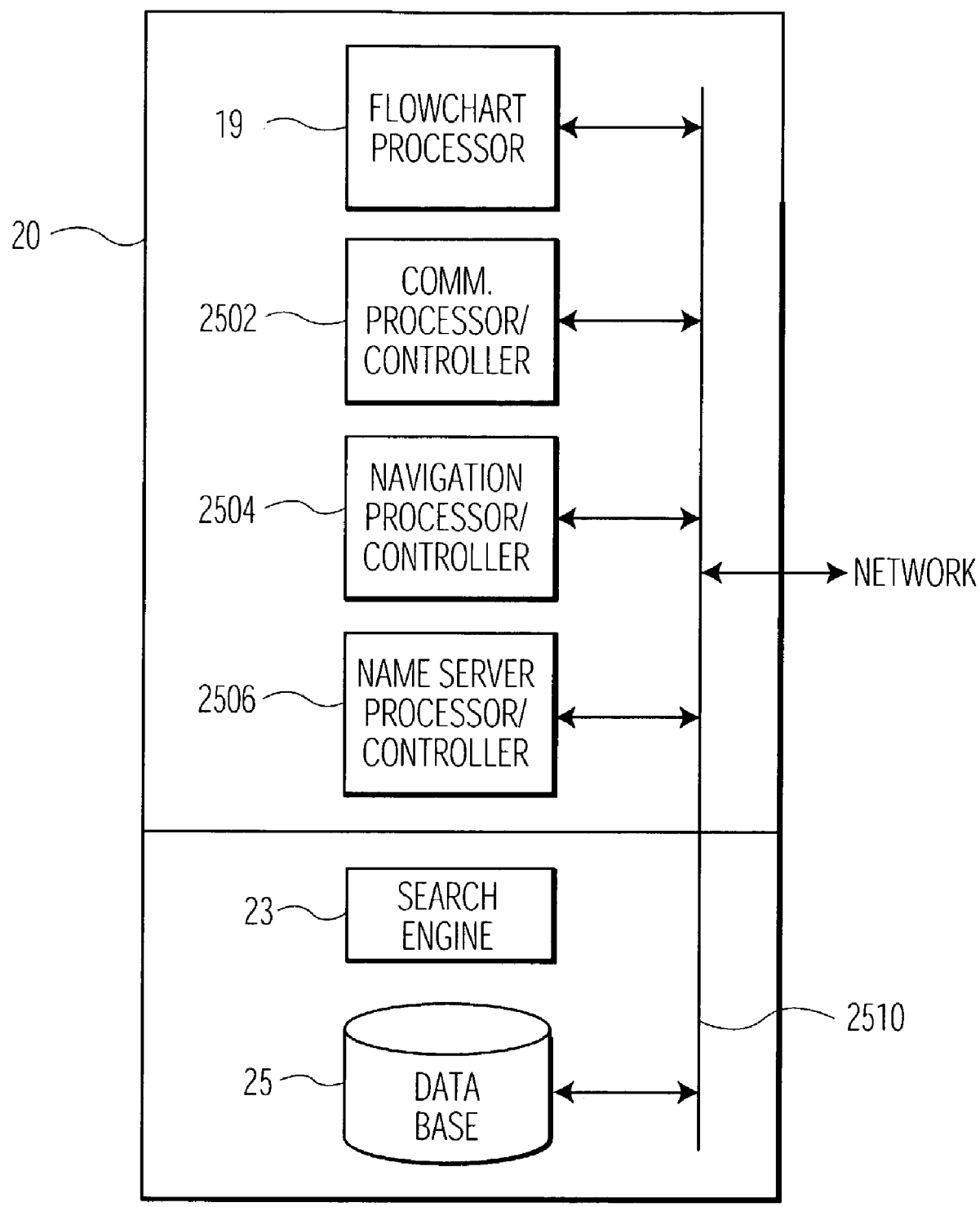
FIG. 11 is a block diagram of a server having functionality in accordance with the principles of the invention.

FIG. 11 shows a block diagram of an exemplary embodiment of server 20 (FIG. 1) including functions in accordance with the present invention for generating data for configuring and presenting a Flowsheet trend indicative display and for managing, collating, searching and updating data base 25 containing patient medical information. Executable applications or processors operative to carry out instructions for performing the various functions described herein include an executable application 19 for performing Flowchart related processing and communications processing module 2502 that acquires the patient data including the monitored parameters allocated to a given patient from the network and collates the information for storage in data base 25. Navigation collation processor 2504 operates in conjunction with the web browser and display generator software to collate and prioritize parameters for display to the user while navigating through various applications selected by a user through the user interface. Name server processor 2506 associates unique identifiers (IDs) with each node connected to the system network and with each patient in the system in order to track and update patient information throughout the system. Input/output data and control signals are used to communicate between the various processors as well as to interface with the data base 25 and search engine 23 and with the network via communication line 2510.

The fluid data derivation and display system, images and processes presented in FIGS. 1-11 are not exclusive. Other display images, systems and processes may be derived in accordance with the principles of the invention to accomplish the same objectives. Although this invention has been described with reference to particular embodiments, it is to be understood that the embodiments and variations shown and described herein are for illustration only and that various modifications may be implemented by those skilled in the art without departing from the scope of the invention. The data extrapolation and interpolation system may be extended to other applications that store burdensome quantities of parameter data.

What is claimed is:

1. A patient medical parameter data processing system for providing patient medical parameter data for trend indicative display covering a time period comprising user selectable patient parameter acquisition time intervals, comprising:
    an acquisition processor for receiving data identifying,
    for a continuing infusion,
        (a) rate of volume of fluid infusion into a patient, a fluid type identifier and a start time and start date of said continuing infusion, and
    for a non-continuing infusion,
        (b) a total volume of fluid infusion, a fluid type identifier and a time and date of said non-continuing infusion; and
    a data processor for determining, from said received data, a cumulative total volume infusion of a particular fluid into a particular patient for a particular user selectable patient parameter acquisition time interval, wherein said data processor stores said received data comprising a reduced set of fluid parameter data supporting extrapolation and interpolation of intermediate fluid volume data values affecting fluid cumulative volume computation and excluding storage of fluid parameter data irrelevant to fluid cumulative volume computation.

2. A data processing system according to claim 1, wherein said reduced set of fluid parameter data supporting interpolation of intermediate fluid volume data values and including
    a generator for generating data representing an image showing a trend indicative display of at least one of, (a) a fluid volume infusion, (b) a net balance of fluid infusion and (c) said cumulative total volume infusion into said particular patient of said particular fluid.

3. A data processing system according to claim 1, wherein in response to user selection of a second acquisition time interval different to said particular user selectable acquisition time interval,
    said data processor automatically determines, from said received data, another cumulative total volume infusion of said particular fluid into said particular patient for said second acquisition time interval.

4. A data processing system according to claim 1, wherein said data processor automatically determines, from said received data, cumulative total volume infusion of said particular fluid into said particular patient for a time period comprising a plurality of user selectable patient parameter acquisition time intervals.

5. A data processing system according to claim 1, wherein in response to user command and entry of data including, for said particular fluid and said particular patient, a volume infusion data value, fluid identifier and at least one of, (i) a rate of a continuing volume fluid infusion into a patient, and a start time and start date of said continuing volume fluid infusion and (ii) a total non-continuing volume fluid infusion, and a time and date of said non-continuing volume fluid infusion,
    said data processor uses said entered data for determining a cumulative total volume infusion of said particular fluid into said particular patient for a particular user selectable patient parameter acquisition time interval.

6. A data processing system according to claim 1, wherein said reduced set of fluid parameter data affects rate of fluid intake or output computation for said particular patient and excluding storage of fluid parameter data irrelevant to rate of fluid intake or output computation.

7. A data processing system according to claim 1, wherein said data processor determines a cumulative total volume infusion of a particular fluid into a particular patient for a time period comprising a plurality of user selectable patient parameter acquisition time intervals.

8. A data processing system according to claim 1, wherein said data processor uses received data to interpolate at least one of,
(a) a cumulative total volume infusion and
(b) a rate of volume of fluid infusion, of a particular fluid into a particular patient for a particular time.

9. A data processing system according to claim 1, wherein said continuing infusion comprises at least one of, (a) a drip medication fluid infusion and (b) a constant rate pump fluid infusion and
said non-continuing infusion comprises at least one of, (i) a bolus, (ii) an injected fluid infusion and (iii) a single manually administered fluid infusion and said non-continuing infusion is administered in a time period substantially shorter than said continuing infusion.

10. A data processing system according to claim 1, wherein said received data comprises a reduced set of received fluid related patient parameter data affecting fluid cumulative volume computation.

11. A patient medical parameter data processing system for providing patient medical parameter data for trend indicative display covering a time period comprising user selectable patient parameter acquisition time intervals, comprising:
an acquisition processor for receiving fluid related patient parameter data from a patient;
a data processor for,
identifying a reduced set of received fluid related patient parameter data supporting interpolation of intermediate fluid volume data values affecting fluid cumulative volume computation and
storing said reduced set of identified fluid related patient parameter data exclusive of fluid parameter data irrelevant to fluid cumulative volume computation, and
determining, from said reduced set of identified fluid related patient parameter data, a cumulative total volume infusion of a particular fluid into a particular patient for a particular user selectable patient parameter acquisition time interval.

12. A data processing system according to claim 11, wherein
said reduced set of identified fluid related patient parameter data supports extrapolation of intermediate fluid volume data values affecting fluid cumulative volume computation.

13. A data processing system according to claim 12, wherein
said data processor automatically determines said cumulative total volume infusion in response to a user command to access a fluid parameter trend indicative display image.

14. A data processing system according to claim 11, wherein
said reduced set of identified fluid related patient parameter data comprises,
for a continuing infusion,
(a) rate of volume of fluid infusion into a patient, a fluid type identifier and a start time and start date of said continuing infusion, and
for a non-continuing infusion,
(b) a total volume of fluid infusion, a fluid type identifier and a time and date of said non-continuing infusion.

15. A user interface system for providing patient medical parameter data for trend indicative display covering a user selectable time period, comprising:
an acquisition processor for receiving data associated with a user selected time period, said received data identifying, for a continuing infusion, a rate of volume of fluid infusion into a patient, a fluid type identifier and a start time and start date of said continuing infusion,
a data processor for determining, from said received data, a cumulative total volume infusion of a particular fluid into a particular patient for said user selected time period, wherein said data processor stores said received data comprising a reduced set of fluid parameter data supporting interpolation and extrapolation of intermediate fluid volume data values affecting fluid cumulative volume computation for a non-continuing infusion including a total volume of fluid infusion, a fluid type identifier and a time and date of said non-continuing infusion and excluding storage of fluid parameter data irrelevant to fluid cumulative volume computation; and
a display generator for initiating generation of data representing an image showing a trend indicative display and indicating said cumulative total volume infusion into a particular patient of a particular fluid for said user selected time period.

16. A user interface system according to claim 15, wherein
said received data includes data identifying, for a non-continuing infusion, a total volume of fluid infusion, a fluid type identifier and a time and date of said non-continuing infusion.

17. A user interface system according to claim 15, wherein
said user selected time period comprises at least one of, (a) a patient parameter acquisition time interval, (b) a plurality of patient parameter acquisition time intervals, (c) an hour (d) a multiple hour interval and (e) a work shift period.

18. A user interface system according to claim 15, wherein
said received data comprises a reduced set of received fluid related patient parameter data affecting fluid cumulative volume computation.

19. A method for providing patient medical parameter data for trend indicative display covering a time period comprising user selectable patient parameter acquisition time intervals, comprising the steps of
receiving data identifying,
for a continuing infusion,
(a) rate of volume of fluid infusion into a patient, a fluid type identifier and a start time and start date of said continuing infusion, and
for a non-continuing infusion,
(b) a total volume of fluid infusion, a fluid type identifier and a time and date of said non-continuing infusion;
determining, from said received data, a cumulative total volume infusion of a particular fluid into a particular patient for a particular user selectable patient parameter acquisition time interval, and
storing said received data comprising a reduced set of fluid parameter data supporting interpolation and extrapolation of intermediate fluid volume data values affecting fluid cumulative volume computation and excluding storage of fluid parameter data irrelevant to fluid cumulative volume computation.

20. A method for providing patient medical parameter data for trend indicative display covering a time period comprising user selectable patient parameter acquisition time intervals, comprising the steps of:

receiving fluid related patient parameter data;

identifying a reduced set of received fluid related patient parameter data supporting interpolation and extrapolation of intermediate fluid volume data values affecting fluid cumulative volume computation and storing said reduced set of identified fluid related patient parameter data exclusive of fluid parameter data irrelevant to fluid cumulative volume computation, and determining, from said reduced set of identified fluid related patient parameter data, a cumulative total volume infusion of a particular fluid into a particular patient for a particular user selectable patient parameter acquisition time interval.

21. A method for providing a patient medical parameter data trend indicative display covering a user selectable time period, comprising the steps of:

receiving data associated with a user selected time period, said received data identifying, for a continuing infusion, a rate of volume of fluid infusion into a patient, a fluid type identifier and a start time and start date of said continuing infusion, determining, from said received data, a cumulative total volume infusion of a particular fluid into a particular patient for said user selected time period, storing said received data comprising a reduced set of fluid parameter data supporting interpolation and extrapolation of intermediate fluid volume data values affecting fluid cumulative volume computation for a non-continuing infusion including a total volume of fluid infusion, a fluid type identifier and a time and date of said non-continuing infusion and excluding storage of fluid parameter data irrelevant to fluid cumulative volume computation and excluding storage of fluid parameter data irrelevant to fluid cumulative volume computation; and initiating generation of data representing an image showing a trend indicative display and indicating said cumulative total volume infusion derived from said reduced set of fluid parameters into a particular patient of a particular fluid for said user selected time period.

* * * * *